US010220000B2

(12) United States Patent
Fologea et al.

(10) Patent No.: US 10,220,000 B2
(45) Date of Patent: *Mar. 5, 2019

(54) METHODS AND COMPOSITIONS FOR X-RAY INDUCED RELEASE FROM PH SENSITIVE LIPOSOMES

(71) Applicant: The Board of Trustees of the University of Arkansas, Little Rock, AR (US)

(72) Inventors: Daniel Fologea, Boise, ID (US); Ralph Henry, Fayetteville, AR (US); Greg Salamo, Fayetteville, AR (US); Yuriy Mazur, Fayetteville, AR (US); Michael J. Borrelli, Little Rock, AR (US)

(73) Assignees: The Board of Trustees of the University of Arkansas, Little Rock, AR (US); BioVentures, LLC, Little Rock, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/847,350

(22) Filed: Dec. 19, 2017

(65) Prior Publication Data

US 2018/0104188 A1 Apr. 19, 2018

Related U.S. Application Data

(63) Continuation of application No. 14/357,038, filed as application No. PCT/US2012/064087 on Nov. 8, 2012, now Pat. No. 9,849,087.

(Continued)

(51) Int. Cl.
*A61K 9/127* (2006.01)
*A61K 9/00* (2006.01)
(Continued)

(52) U.S. Cl.
CPC .......... *A61K 9/1271* (2013.01); *A61K 9/0009* (2013.01); *A61K 45/06* (2013.01); *A61K 47/10* (2013.01); *A61N 5/10* (2013.01)

(58) Field of Classification Search
CPC ..................................... A61K 9/127
See application file for complete search history.

(56) References Cited

U.S. PATENT DOCUMENTS

| 4,921,757 A | 5/1990 | Wheatley et al. |
| 4,981,985 A | 1/1991 | Kaplan et al. |

(Continued)

FOREIGN PATENT DOCUMENTS

| EP | 0312212 | 4/1989 |
| EP | 2255790 | 12/2010 |

(Continued)

OTHER PUBLICATIONS

Andrews, H.L. et al. (1950). "X-ray Dose Determinations with Chloral Hydrate." The Journal of Chemical Physicis 18(9): 1165-1168.

(Continued)

*Primary Examiner* — Gollamudi Kishore
(74) *Attorney, Agent, or Firm* — Andrus Intellectual Property Law, LLP

(57) ABSTRACT

Compositions including pH sensitive lipid vesicles comprised of a lipid layer, an agent, and an organic halogen such that the agent is released from the vesicles after exposure to ionizing radiation. Methods of delivering the agent to a target in a subject using the compositions provided herein are also described. The methods allow for controlled release of the agent. The timing of release of the agent from the lipid vesicle may be controlled as well as the location of release by timing and localizing the exposure to ionizing radiation exposure.

19 Claims, 2 Drawing Sheets

Related U.S. Application Data

(60) Provisional application No. 61/556,936, filed on Nov. 8, 2011.

(51) Int. Cl.
  *A61K 45/06* (2006.01)
  *A61K 47/10* (2017.01)
  *A61N 5/10* (2006.01)

(56) References Cited

U.S. PATENT DOCUMENTS

| | | | |
|---|---|---|---|
| 5,283,122 | A | 2/1994 | Huang et al. |
| 5,366,881 | A | 11/1994 | Singh et al. |
| 5,753,261 | A | 5/1998 | Fernandez et al. |
| 5,770,222 | A | 6/1998 | Unger et al. |
| 5,820,879 | A | 10/1998 | Fernandez et al. |
| 5,827,531 | A | 10/1998 | Morrison et al. |
| 5,876,747 | A | 3/1999 | Stracher et al. |
| 5,891,465 | A | 4/1999 | Keller et al. |
| 5,891,689 | A | 4/1999 | Takle et al. |
| 5,955,365 | A * | 9/1999 | Szoka, Jr. ............ A61K 9/1271 424/450 |
| 6,099,864 | A | 8/2000 | Morrison et al. |
| 6,159,443 | A | 12/2000 | Hallahan |
| 6,277,610 | B1 | 8/2001 | Grae |
| 6,426,086 | B1 | 7/2002 | Papahadjopoulos et al. |
| 6,562,316 | B1 | 5/2003 | Edwards et al. |
| 6,576,257 | B1 | 6/2003 | Yarmut |
| 6,579,706 | B2 | 6/2003 | Grae |
| 6,602,274 | B1 | 8/2003 | Chen |
| 6,835,394 | B1 | 12/2004 | Discher et al. |
| 6,989,153 | B2 | 1/2006 | O'Brien et al. |
| 7,018,395 | B2 | 3/2006 | Chen |
| 7,049,140 | B1 | 5/2006 | Hallahan |
| 7,132,289 | B2 | 11/2006 | Kobayashi et al. |
| 7,186,399 | B2 | 3/2007 | Lanza et al. |
| 7,223,600 | B2 | 5/2007 | Berg et al. |
| 7,273,620 | B1 | 9/2007 | Zhigaltsev et al. |
| 7,285,536 | B2 | 10/2007 | Cahalon et al. |
| 7,655,468 | B2 | 2/2010 | Huang et al. |
| 7,951,846 | B2 | 5/2011 | Bae et al. |
| 8,808,733 | B2 | 8/2014 | Fologea et al. |
| 9,849,087 | B2 | 12/2017 | Fologea et al. |
| 2002/0064554 | A1 | 5/2002 | O'Brian et al. |
| 2002/0115219 | A1 | 8/2002 | Kobayashi et al. |
| 2002/0168734 | A1 | 11/2002 | Grae |
| 2003/0219785 | A1 | 11/2003 | Hallahan et al. |
| 2004/0023351 | A1 | 2/2004 | Grae |
| 2004/0096425 | A1 | 5/2004 | Hogset et al. |
| 2004/0110835 | A1 | 6/2004 | Keller |
| 2004/0215292 | A1 | 10/2004 | Chen |
| 2005/0075268 | A1 | 4/2005 | Berg et al. |
| 2005/0186264 | A1 | 8/2005 | Kiani et al. |
| 2005/0196401 | A1 | 9/2005 | Chen |
| 2005/0214356 | A1 | 9/2005 | Joyce |
| 2005/0272677 | A1 | 12/2005 | Friesen et al. |
| 2006/0024359 | A1 | 2/2006 | Walker et al. |
| 2006/0099141 | A1 | 5/2006 | O'Brian et al. |
| 2006/0159739 | A1 | 7/2006 | Lasic et al. |
| 2006/0188442 | A1 | 8/2006 | Hallahan |
| 2006/0210549 | A1 | 9/2006 | Srvastava et al. |
| 2006/0292211 | A1 | 12/2006 | Hood et al. |
| 2007/0054873 | A1 * | 3/2007 | MacLachlan ........ A61K 31/573 514/44 R |
| 2007/0274953 | A1 | 11/2007 | Berg et al. |
| 2007/0292495 | A1 | 12/2007 | Ludwig et al. |
| 2008/0293924 | A1 | 11/2008 | Menart et al. |
| 2008/0311182 | A1 | 12/2008 | Ferrari et al. |
| 2009/0304589 | A1 | 12/2009 | Bondurant et al. |
| 2010/0009926 | A1 | 1/2010 | Kim et al. |
| 2010/0129430 | A1 | 5/2010 | Sofou |
| 2011/0027171 | A1 | 2/2011 | Stavroula |
| 2011/0052671 | A1 | 3/2011 | Zasadzinski et al. |
| 2012/0141381 | A1 * | 6/2012 | Dewhirst ............... A61K 9/127 424/9.321 |

FOREIGN PATENT DOCUMENTS

| | | | |
|---|---|---|---|
| EP | 2509604 | | 10/2012 |
| JP | 2009/114167 | * | 5/2009 |
| JP | 2009114167 | | 5/2009 |
| WO | WO 1990005147 | | 5/1990 |
| WO | WO 2010129686 | | 11/2010 |

OTHER PUBLICATIONS

Bennett, D.E., et al., "Photoactivated enhancement of liposome fusion," Biochemistry (1995) 34(9):3102-3113.

Bisby, R.H. et al., "Fast laser-induced solute release from liposomes sensitized with photochromic lipid: effects of temperature, lipid host, and sensitizer concentration," Biochem Biophys Res Commun (1999) 262(2):406-410.

Bisby, R. et al. (1999) "Photosensitive liposomes as 'cages' for laser-triggered solute delivery: the effecr of bilayer cholesterol on kinetics of solute release." FEBS Letters 463: 165-168.

Bisby, R. et al. (2000). "Active Uptake of Drugs into Photosensitive Liposomes and rapid release on UV Photolysis." Photochemistry and Photobiology 72(1):57-61.

Bisby, R. et al. (2000). "Wavelength-Programmed Solute Release from Photosensitive Liposomes." Biochemical and Biophysical Research Communications. 276: 169-173.

Bondurant, B. et al., "Photoinitiated destabilization of sterically stabilized liposomes," Biochim Biophys Acta (2001) 1511(1):113-122.

Braem, et al., "Observation of the UV scintillation light from high energy electron showers in liquid Xenon," European Organization for Nuclear Research (1992) CERN-PPE/92-36 (Abstract) http://cdsweb.cem.ch/record/234171/files/cer-000148810.pdf.

Brown, E. B., et al., "Photolysis of caged calcium in femtoliter volumes using two-photon excitation," Biophysical Journal (1999) 76:489-499.

Carles, A.G., Radiation Protection Dosimetry, 122(1-4), 420-426, 2006.

Chen, W. et al., "Using nanoparticles to enable simultaneous radiation and photodynamic therapies for caner treatment," Journal of Nanoscience and Nanotechnology (2006) 6:1159-1166.

Chen, W., et al., "Structure and luminescence of BaFBr:Eu2+ and BaFBr:Eu2+,Tb3+ phosphors and thin films," Journal of Applied Physics (2005) 97:083506-1-083506-8.

Chen, W., et al., "Utilizing nanofabrication to construct strong, luminescent materials," Nanotechnology (2006) 17:2595-2601.

Connor, J., Yatvin, M., Huang, L., "pH-sensitive liposomes: Acid-induced liposome fusion." PNAS, 81, 1715-1718, 1984.

Dai, S., et al., "pH-Responsive polymers: synthesis, properties and application," Soft Matter (2008) 4: 435-449.

Davidsen, J., et al., "Secreted phospholipase A2 as a new enzymatic trigger mechanism for localised liposomal drug release and absorption in diseased tissue," Biochimica et Biophysica Acta (2003) 1609:95-101.

Ellis-Davies, G. C. R., et al., "Tuning caged calcium:Photolabile analogues of EGTA with improved optical and chelation properties," Cell Calcium (2006) 39:75-83.

Freeman, G.R., Van Cleave, A.B., Spinks, J.W.T, "Irradiation of One Molar Aqueous Chloral Hydrate Solution with Co60-Gamma-Rays and Betatron X Rays." Canadian Journal of Chemistry, 31, 1164-1172, 1953.

Freeman, G.R., Van Cleave, A.B., Spinks, J.W.T., "Irradiation of Aqueous Chloral Hydrate Solutions with Co60 Gamma-Rays." Canadian Journal of Chemistry, 32, 322-326, 1953.

Hafez, I.M., Ansell, S., Cullis, P.R., Biophys. J., "Tunable pH-Sensitive Lipsomes Composed of Mixtures of Cationic and Anionic Lipids." 79, 1438-1446, 2000.

Harrington, K. et al. (2000). "Pegylated Liposome-encapsulated Doxorubicin and Cisplatin Enhance the Effect of Radiotherapy in a Tumor Xenograft Model." Clinical Cancer Research 6:4939-4949.

Hazemoto, N. et al. (1990). "pH-Sensitive Liposomes Composed of Phosphatidylethanolamine and Fatty Acid." Chem. Pharm. Bull. 38(3):748-751.

(56) References Cited

OTHER PUBLICATIONS

Heusinger, H., Woods, R.J., Spinks, J.W.T, "Study of the Padiolysis of Bromal Hydrate Solutions Using C14-labelled bromal." Canadian Journal of Chemistry, 37(7), 1127-1131, 1959.

Hilsenrod, A. (1956). "Irradiation of Chloral Hydrate Solutions." Journal of Chemical Physics 24:917-918.

Hiraka, K., Kanehisa, M., at al, "Preparation of pH-sesnitive liposomes retaining SOD mimic and their anticancer effect." Colloids and Surfaces B: Biointerfaces, 67, 54-58, 2008.

Hitzman, C.J. et al. (2006) "Development of a respirable, sustained release microcarrier for 5-fluorouracil II: in vitro and in vivo optimization of lipid coated nanoparticles." Journal of Pharmaceutical Sciences 95(5):1127-1143.

Immordino, M.L. et al. (2006) "Stealth liposomes: review of the basic science, rationale, and clinical applications, existing and potential." International Journal of Nanomedicine 1(3):297-315.

Jensen, S. S., et al., "Secretory phospholipase A2 as a tumor-specific trigger for targeted delivery of a novel class of liposomal prodrug anticancer either lipids," Molecular Cancer Therapeutics (2004) 3(11):1451-1458.

Kitano, H. et al. (1991). "pH-responsive liposomes which contain amphiphiles prepared by using lipophilic radical initiator." Macromolecules 24(1):42-46.

Lamparski, H. et al., "Photoinduced destabilization of liposomes," Biochemistry (1992) 31(3):685-694.

Lee, R.J. et al. (1998). "The Effects of pH and Intraliposomal Buffer Strength on the rate of Liposome Content Release and Intracellular Drug Delivery." Bioscience Reports 18(2):69-78.

Leroux, J.C., Advanced Drug Delivery Reviews, 56, 925-926, 2004.

Liu, Y., et al., "Investigation of water-soluble x-ray luminescence nanoparticles for photodynamic activation," Applied Physics Letters (2008) 92:043901-1-043901-3.

Liu, Y., et al., "X-ray luminescence of LaF3:Tb3+ and LaF3:Ce3+,Tb3+ water-soluble nanoparticles," Journal of Applied Physics (2008) 103:063105-1-063105-7.

Lokling, K-E., Skurtveit, R., at al, "Tuning the MR properties of blood-stable pH-responsive paramagnetic liposomes."International Journal of Pharmaceutics, 274, 75-83, 2004.

Lokling, K-E., Skurtveit, R., at al, "pH-sesnitive paramagnetic liposomes for MRI: assessment of stability in blood." Magnetic Resonance Imaging, 21, 531-540, 2003.

Miller, C.R. et al., "Effect of liposomal composition on photoactivated liposome fusion," Biochemistry (1996) 35(36): 11782-11790.

Miller, C.R. et al., "Visible light-induced destabilization of endocytosed liposomes," FEBS Lett. (2000) 467(1):52-56.

Morgan, C.G., et al., "Fast solute release from photosensitive liposomes: an alternative to 'caged' reagents for use in biological systems," FEBS Lett. (1995) 375(1-2):113-116.

Platford, R.F., Spinks, J.W.T, "Irradation of Aqueous Chloral Hydrate with Sr90—Yr90 Beta Rays." Canadian Journal of Chemistry, 37, 1022-1028, 1959.

Renner, L., Osaki, T., et al,"Supported Lipid Bilayers on Spacious and pH-Responsive Polymer Cushions with Varied Hydrophilicity," J. Phys. Chem. B, 112, 6373-6378, 2008.

Rosenthal, D.J. et al. (2002) "A phase I study of SPI-077 (Stealth liposomal cisplatin) concurrent with radiation therapy for locally advanced head and neck cancer." Investigational New Drugs 20(3):343-349.

Sheng Dai, palaniswamy Ravi, kam Chiu Tam, Soft Matter, 435-449, 2008.

Slepuskin, V.A., Simoes, S., et al, "Sterically Stabilized pH-sensitive Liposomes." The Journal of Biol. Chem., 272, 2382-2388, 1997.

Spratt, T. et al., "Rapid release of liposomal contents upon photoinitiated destabilization with UV exposure," Biochim Biophys Acta (2003) 1611(1-2):35-43.

Trosko, J.E. et al. (2001) Mutation Research 480-481:219-229.

Wang, F. et al., "Facile synthesis of water-soluble LaF3:Ln3+ nanocrystals," J. Material Chemistry (2006) 16:1031-1034.

Woods, R.J., Spinks, J.W.T., "The Action of Co60 Gamma Rays and of Fenton Reagent on Aqueous Bromal Hydrate Solutions." Canadian Journal of Chemistry, 35, 1475-1486, 1957.

Woods R.J, Spinks, J.W.T, "The Radiolysis of Some Organic Halogen Compounds in Aqueous Solution." Canadian Journal of Chemistry, 38, 77-93, 1960.

International Search Report and Written Opinion for International Patent Application No. PCT/US2010/029413 dated Jun. 1, 2010 (11 pages).

International Search Report and Written Opinion for PCT/US12/64087 dated Jan. 11, 2013 (8 pages).

Extended European Search Report for EP2776013 dated Apr. 28, 2015 (9 pages).

European Exam Report for EP2776013 dated Feb. 6, 2018 (7 pages).

Office Action for U.S. Appl. No. 14/357,038 dated Jan. 26, 2017 (14 pages).

Office Action for U.S. Appl. No. 14/357,038 dated May 30, 2017 (17 pages).

* cited by examiner

METHODS AND COMPOSITIONS FOR X-RAY INDUCED RELEASE FROM PH SENSITIVE LIPOSOMES

CROSS-REFERENCE TO RELATED APPLICATIONS

This patent application is a continuation application of U.S. patent application Ser. No. 14/357,038, filed May 8, 2014 and issuing as U.S. Pat. No. 9,849,087 on Dec. 26, 2017, which is a national stage filing under 35 U.S.C. 371 of International Application No. PCT/US2012/064087, filed Nov. 8, 2012, which claims the benefit of priority of U.S. Provisional Patent Application No. 61/556,936, filed Nov. 8, 2011, the contents of each are incorporated herein by reference in their entirety.

INTRODUCTION

Current approaches to treatment of cancer and other disorders may include combinations of local therapies, such as surgery and radiation therapy, with systemic therapies, such as chemotherapy and administration of pharmaceuticals or other agents. The therapeutic success of any treatment is proportional to the delivered dose of the pharmaceutical or other agent to the site in the subject where the cancer or disorder is localized. The dose is limited by toxicity to normal tissue and delivery to the affected site in the subject.

Controlled drug release is one method of allowing the use and specific delivery of increased doses of the pharmaceutical or other agent to the affected site in the subject while limiting toxicity caused by the pharmaceutical or agent. Despite numerous advances in the area of controlled drug release to increase delivery of pharmaceuticals and other agents to affected sites in a subject and to release the agents at the affected site in a controlled manner, sufficient localized release of the agents to a localized affected site remains problematic.

SUMMARY

Compositions for controlled drug release and methods of using these compositions are provided herein. The compositions are based on pH sensitive liposomes which are capable of releasing a therapeutic agent at a target location and in a controllable manner. In particular, compositions comprising a pH sensitive lipid vesicle comprising an agent and an organic halogen are provided herein. The pH sensitive lipid vesicle is constructed such that exposure of the composition to ionizing radiation allows the agent to be released from the lipid vesicle. The agent may be released in a controllable fashion and in a localized manner depending on the amount of organic halogen incorporated into the pH sensitive lipid vesicle and the intensity, duration and localized use of ionizing radiation.

In another aspect, pharmaceutical compositions comprising the pH sensitive lipid vesicles described herein and a pharmaceutically acceptable carrier are provided.

In another aspect, methods of delivering an agent to a target in a subject are provided. These methods include administering the pH sensitive lipid vesicle described herein to the subject and then exposing the target to ionizing radiation, whereby the agent is released from the lipid vesicle near the target in the subject.

In still another aspect, methods of controlled drug release are provided in which the pH sensitive lipid vesicles described herein are administered to the subject and a localized area of the subject is exposed to ionizing radiation causing the agent to be released in a localized area.

In a further aspect, methods of treating a condition are provided. The methods include administering the pH sensitive lipid vesicles described herein to a subject with the condition and exposing a portion of the subject to ionizing radiation. The agent is capable of treating the condition and is released from the lipid vesicle in the portion of the subject exposed to ionizing radiation. Suitably the portion of the subject exposed to ionizing radiation is the portion of the subject in which the condition is in need of treatment with the agent. In one aspect, such a treatment moderates or reduces at least one toxic or negative side effect associated with treatment with the agent.

BRIEF DESCRIPTION OF THE DRAWINGS

FIG. 2A shows the results using liposomes containing 1 M chloral hydrate. FIG. 2B shows the results using liposomes containing 0.5 M chloral hydrate. FIG. 2C shows the results using liposomes containing 0.1 M chloral hydrate. In all three graphs, squares represent release from liposomes after no irradiation exposure. The triangles and circles represent the release of the fluorescent marker from the liposomes after exposure to X-rays. The triangles represent liposomes that also contained 0.1 M glucose in the vesicles.

DETAILED DESCRIPTION

Figure 1:
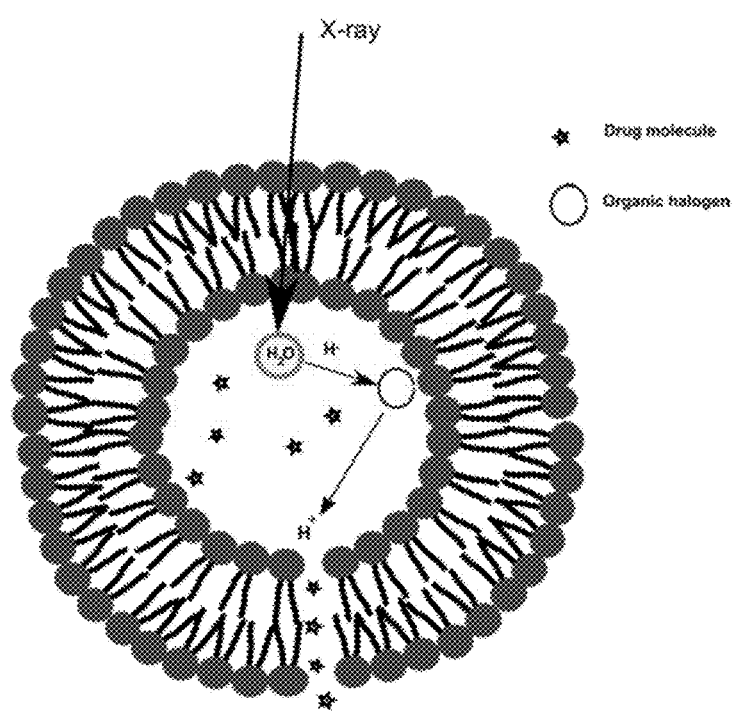
FIG. 1 is a schematic diagram of a method for controlled drug release based on a pH sensitive lipid vesicle. A lipid vesicle comprising pH sensitive components, such as lipids or polymers, an aqueous environment, an agent and an organic halogen is depicted. When exposed to ionizing radiation, such as X-rays, the organic halogen reacts with water in the lipid vesicle to release H+, decrease the pH inside the vesicle and cause the pH sensitive lipid vesicle to become permeable and release the agent.

The ability to release a therapeutic drug only at a desired location and in a controllable manner is a crucial step in limiting the potential harmful systemic sequels inherent to non-localized drug delivery. This challenge is yet unmet especially for cancer therapy where the chemical dose is drastically limited by the remote toxicity. Ideally, a drug delivery method would comprise drug transportation to the desired site in a specialized vehicle which protects the drug from acting until an external controlled stimulus triggers the drug release at the target site. Stealth liposomes are a good example of a vehicle that can carry drug cargo in a protected state and evade detection by the body's self defense mechanisms. However, the contained drug is not quickly released only at the desired site and in a controllable manner. Local and controlled drug release is a major challenge for drug therapy and various approaches have been proposed to solve this issue.

One approach for drug delivery makes use of photo sensitive liposomes, which release the trapped drug upon UV photolysis (Bisby et al. 1999; Bisby et al. 2000; Bisby et al. 2000). Photoisomerization drives the photochromic lipid to a bulky state which destabilizes the bilayer and increases its permeability for the entrapped drug. Although very promising, this approach has limits imposed by the use of UV light as activator. The human body is not transparent to UV radiation. The second drawback is given by the high energy requirements for the UV laser pulse (cca 15 mJ/10 nsec). Another approach is described in International Application No. PCT/US2010/029413, which is incorporated by reference herein in its entirety.

pH sensitive liposomes are one of the most studied and promising approaches for drug delivery (Hazemoto et al. 1990; Kitano et al. 1991; Slepushkin et al. 1997; Lee et al. 1998; Hafez et al. 2000). pH sensitive liposomes are able to deliver their payload as a result of the variation of the internal or external pH, which destabilizes the membrane and increases the permeability for the entrapped drug. A second drug delivery mechanism is represented by their ability to fuse when exposed to the appropriate pH. Although it has been supposed that the intra-tumor pH has lower values and this is one of the main mechanisms of targeted drug release from these liposomes, this assumption has never been satisfactorily proved. Use of pH sensitive liposome to deliver agents to tumor tissues has not been widely demonstrated. On the other hand, the internal pH suffers from variability, and the release rate can be extremely low in many conditions. Moreover, the pH sensitive liposomes can be potentially used only if the diseased site (or the desired location) experiences strong enough pH changes.

The pH sensitive lipid vesicles described herein utilize ionizing radiation to trigger release of the agent only at the irradiated site. The described controlled drug delivery scheme makes use of pH sensitive liposomes loaded with an agent and an organic halogen. The liposomes or lipid vesicles are designed to release the agent upon interaction with highly localized therapeutic X-ray radiation. In particular, the actinic beam will be used to control the pH inside the liposomes. A decrease in pH inside the vesicle will be triggered due to the aqueous solution of organic halogens inside the vesicle yielding an increased acidity upon interaction with ionizing radiation (Andrews and Shore 1950; Freeman et al. 1953; Freeman et al. 1953; Andrews et al. 1957; Woods and Spinks 1957; Heusinger et al. 1959; Platford and Spinks 1959; Woods and Spinks 1960).

Briefly, the agent and a radiation sensitive compound (such as an organic halogen) are encased in the water interior of a pH sensitive lipid vesicle such as a liposome. The free radicals released by radiolysis interact with the organic halogen and increase the acidity, i.e. free protons, inside the vesicles. The protons interact with the pH sensitive components in the lipid membrane (lipids and/or polymers) and the agent is released as a consequence of the increased permeability of the membrane.

Thus the lipid vesicles described herein may be administered to a subject and the agent may be sequestered within the lipid vesicle until the subject or a target area on or in the subject is exposed to ionizing radiation, thereby effecting release of the agent from the lipid vesicle in a subject or in a target area of the subject. The compositions may be used for controlled release of the agent to a target, such as a target tissue, in a localized area. For example, the compositions may be used to deliver an agent to a tumor, damaged tissue, site of infection or site of inflammation.

The lipid vesicles encasing all the components required for drug delivery can have a variety of compositions and internal aqueous contents. The lipid vesicles can be micelles, microspheres or liposomes. Liposomes may be unilamellar or multilamellar. The lipid vesicles are suitably unilamellar, sterically stabilized, stealth, size adjusted for a reduced absorption by the mononuclear phagocyte system (MPS), and the lipidic phase should contain lipids or polymers assuring pH sensitivity. The lipid vesicles may be made of any suitable lipid, including but not limited to, polar lipids, such as phospholipids, such as phosphoglycerides, such as phosphatidylethanolamine, phophatidylcholine, phosphatidylserine, cardiolipin, palmitoylhomocysteine, cholesterol or combinations thereof. Other lipid moieties may also be included in the lipid vesicles such as triacylglycerols, waxes, sphingolipids, and sterols and their fatty acid esters, or combinations thereof. The lipid vesicle's lipid layer may also include polypeptides, such as transmembrane polypeptides, protein channels or other polypeptides capable of associating with or localizing to the lipid layer.

The lipid vesicles are pH sensitive lipid vesicles. Those of skill in the art will appreciate many pH sensitive lipids and pH sensitive polymers are available to generate pH sensitive lipid vesicles. The pH sensitive lipids may include, but are not limited to phosphatidylethanolamine, palmitoylhomocysteine or analogs or derivatives thereof, such as dioleoylphosphatidylethanolamine. pH sensitive polymers may include a pH sensitive moiety including, but not limited to alklyacrylic acid, ethylacrylic acid, propylacrylic acid, butylacrylic acid, and methylacrylic acid. See U.S. Pat. Nos. 7,951,846, 7,655,468, 7,186,399, 6,426,086 and 5,283,122 and U.S. Patent Publication Nos. 20110027171, 20100129430, and 20100009926. The pH sensitive lipids or polymers may be included in the lipid vesicle at between 1 and 25 mol %, suitably 2-20 mol %, suitably 2-5 mol %. The actual composition and lipid ratio in the pH sensitive lipid vesicles may be varied and should be chosen in such a way as to initiate a sustained release at the achieved pH while sealing at the initial pH.

The lipid vesicles may additionally include a functional group such as a targeting molecule or polyethylene glycol. The targeting molecule or polyethylene glycol may be exposed on or attached to the outer surface of the liposome to target the lipid vesicle to a specific tissue or to increase the half-life of the lipid vesicle after administration to a subject. The targeting molecule may be a polypeptide or protein. Suitable targeting molecules include, but are not limited to, an antibody, a receptor such as the folate receptor or a ligand for a receptor that helps target the lipid vesicle to a specific tissue. The targeting molecule may be attached to the outer surface of the lipid vesicle, be a peripheral or integral membrane protein or may be attached by other means known to those skilled in the art such as myristoylation, acetylation, prenylation, palmitoylation, glycosylphosphatidyinositol (GPI) anchors or via cholesterol.

The liposome may be made by any method, including those known to those skilled in the art, such as sonication, extrusion, reverse phase evaporation, the infusion procedure, detergent dilution and the Mozifari method. Suitably the lipid vesicles are made by extrusion. In the Examples, the liposomes were made by extrusion. Suitably, the liposomes are at least about 20 nm, 100 nm, 200 nm, 250 nm in diameter. Suitably the liposomes are no larger than about 400 nm, 500 nm, 1 micron, 2 microns or 4 microns in diameter. The size of the liposome may depend on its selected use. Suitably, the liposomes are of a size such that they are capable of selectively extravagating from leaky blood vessels near a tumor site or a site of inflammation.

The radiation sensitive compound, suitably an organic halogen, should be added in the desired concentration during preparation of the lipid vesicles. The agent can be added during lipid vesicle preparation (passive loading) or after preparation (active or passive loading). The unincorporated components can be removed by centrifugation, dialysis, gel column filtration, etc. The lipid vesicles suitably are prepared with and contain an aqueous media. The aqueous medium can be water or water-based and may also contain salts, sugars, such as glucose, or other additives that may serve to stabilize the vesicle, make the vesicle more pH sensitive or affect the activity of the agent.

The agent controlled release process is initiated by ionizing radiation interacting with water in the aqueous media of the lipid vesicle. Without being bound by theory, the primary interaction takes place between X-ray photons and water, and the Compton Effect dominates in this energy range for low Z. Organic halogen compounds, such as chloral hydrate, are some of the most sensitive to ionizing radiation. The hydrogen halide formed in high yield acidifies the aqueous solution of the lipid vesicle by decreasing the pH. The acid formation is dependent on the organic halogen concentration, radiation dose amount, radiation dose time of exposure, and temperature. Those of skill in the art will understand that the concentration and ionizing radiation dose will depend on the tissue being treated, agent being delivered and subject as well as other factors. The radiolysis of organic halogenated compounds in aqueous solution is a chain reaction; it has been extensively proved that the interaction with radiation results in the formation of hydrogen halide and the acid produced modulates the solutions' pH. The reaction mechanisms and the reaction products (other than acids) are not known in detail but the action is undoubtedly indirect, through the radicals produced in water by the actinic beam. The energy loss in the therapeutic energy range for water solutions is due entirely to the Compton effect; the high yield of the acid formation (at least 100 molecules/ion pair) can be explained only if we account for a chain reaction in the acid formation mechanism. This high yield is essential in modulating the internal pH of liposomes using rather modest radiation doses. The acid produced can decrease the solution pH by a few units, more than enough to destabilize the lipid bilayer and release the agent, or to deliver the agent by promoting the fusion of the pH sensitive liposomes with cells. In the Examples, 6 MeV X-ray, 400 Rad, 2 minutes duration was sufficient to mediate release of the agent from liposome comprising 0.1M to 1M chloral hydrate. Those of skill in the art will understand that the amount of agent released within a particular time after exposure to radiation will be related to the particular dose of ionizing radiation provided and the amount of organic halogen incorporated in the liposome along with other factors. Doses of radiation may be any dosage used to treat individuals without causing undue toxicity. Suitably the dose of radiation may be between 200 and 600 Rad.

The radiation sensitive agent used herein is suitably an organic halogen. The organic halogens suitable for use include but are not limited to chloral hydrate, fluoral hydrate, or bromal hydrate (Woods and Spinks 1957; Heusinger, Woods et al. 1959; Woods and Spinks 1960). The amount of organic halogen added to the lipid vesicles is dependent on the pH necessary to allow permeabilization of the lipid vesicle and the dose of ionizing radiation that will be used. Generally a lower amount of organic halogen will lead to a lower change in pH in the lipid vesicle after exposure to ionizing radiation. In the Examples, 0.1 M to 1 M chloral hydrate was added to the liposomes. Suitably the amount of organic halogen added is between 0.01 M and 2M, suitably from 0.1 to 1M. As demonstrated in the Examples glucose can be added to the lipid vesicle to increase the efficiency of release from the vesicles. Glucose can be added between 0.01 M and 1 M. Suitably glucose is added at between 0.1 M and 1 M.

The agent contained within the lipid vesicles may be any suitable pharmaceutical or other active agent, including but not limited to, chemotherapeutic agents, toxins, radiotherapeutic agents, radiosensitizing agents, imaging agents, tracking agents, antimicrobials, anti-inflammatory agents, polypeptides such as recombinant proteins, cytokines or antibodies, small chemicals or any combination thereof. In alternative embodiments, the active agent may be an angiogenesis inhibitor or an apoptosis inducer.

Illustrative anticancer drugs that may be administered according to the present invention include acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol (soluble), beta-2'-deoxythioguanosine, bisantrene HCL, bleomycin sulfate, busulfan, buthionine sulfoximine, BWA 773U82, BW 502U83.HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflornithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride. Flavone acetic acid, floxuridine, fludarabine phosphate, 5-fluorouracil, Fluosol®, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures thereof.

Exposure of the compositions described herein to ionizing radiation allows the agent to be released from the lipid vesicles by decreasing the pH and causing the lipid vesicle to become permeable as described above. Suitably, exposure of the lipid vesicles to ionizing radiation releases at least 25% of the agent within 4 hours after exposure. More suitably, exposure of the lipid vesicle to ionizing radiation releases at least 50% of the agent within 8 hours after exposure. More suitably, exposure of the lipid vesicle to ionizing radiation releases at least 75% of the agent within 8 hours after exposure. More suitably, exposure of the lipid vesicle to ionizing radiation releases at least 90% of the agent within 8 hours after exposure.

The lipid vesicle compositions described herein may be used to make pharmaceutical compositions. Pharmaceutical compositions comprising the compositions described above and a pharmaceutically acceptable carrier are also provided. A pharmaceutically acceptable carrier is any carrier suitable for in vivo administration. Examples of pharmaceutically acceptable carriers suitable for use in the composition include, but are not limited to, water, buffered solutions, saline, glucose or dextrose solutions, glycerol, oil-based or bacterial culture fluids. Additional components of the compositions may suitably include, for example, excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying. The composition may also be prepared in conventional forms, either as a liquid solution or suspension or in a solid form suitable for preparation as a solution or suspension in a liquid prior to injection, or as an emulsion.

Methods of delivering an agent to a target in a subject are also provided. The methods include administering the lipid vesicles described herein to a subject and exposing the target to ionizing radiation. The ionizing radiation and the organic halogen interact to reduce the pH of the lipid vesicle and destabilize or increase the permeability of the lipid vesicle resulting in the release of the agent from the lipid vesicle at the target site to result in controlled delivery of the agent to the target. The target may be a specific tissue or organ such as the liver, kidneys, spleen or may be the site of a tumor, infection, inflammation or other site of disease. Suitably, the lipid vesicle is administered prior to administration of the ionizing radiation. Suitably, the ionizing radiation source is X-rays as used in the Examples. Other suitable sources of ionizing radiation include gamma-rays and beta-rays. Proton therapy is a promising approach for cancer therapy and proton therapy will also provide a useful source of ionizing radiation. The methods include methods of controlled drug release in which the agent is released from the lipid vesicles in a localized area within the subject and/or at a specific time.

Methods of treating a condition, suitably a medical condition, by administering the lipid vesicle compositions described herein to a subject in need of treatment for the condition. The subject or a portion of the subject is then exposed to ionizing radiation. The agent is capable of treating the condition when released from the pH sensitive lipid vesicle in the portion of the subject exposed to ionizing radiation. By releasing the agent only in or near the portion of the subject exposed to ionizing radiation, the dose of the agent may be increased locally without adverse side-effects that may be associated with treatment with the agent systemically. Thus agents whose side-effects limit the effective dosage range may be used at higher effective doses in combination with the pH sensitive lipid vesicles described herein. Alternatively, many agents have adverse side-effects that are not associated with the effectiveness of the agent. The methods described herein may result in decreased side-effects associated with treatment with the agent.

The lipid vesicle or liposome is generally administered to the subject prior to administration of the ionizing radiation, which triggers release of the active agent, but the compositions and ionizing radiation may be administered simultaneously in certain circumstances. Suitably the lipid vesicle or liposome is administered at 10 minutes, 30 minutes, 1 hour, 2 hours, 4 hours, 8 hours, 24 hours, 48 hours, 3 days, 4 days, 5 days, 6 days or up to 7 days prior to administration of ionizing radiation. The compositions may be administered locally or systemically. The lipid vesicle may be administered by any means available, including those known to those skilled in the art, such as intravenous, intratumoral, intraperitoneal, intramuscular, intra-arterial, intraventricular, subcutaneous, dermal, or transdermal delivery. The lipid vesicle may be exposed to ionizing radiation by exposing the subject or a part of the subject to the radiation. Suitably, the agent is administered in an amount effective to treat the condition and achieve a therapeutic effect in the subject, e.g., an antineoplastic effect.

The methods may be used to treat subjects having one or more of a wide variety of medical conditions, including but not limited to cancer, such as meningiomas, hepatic cell carcinoma, pancreatic tumors, infectious diseases including fungal, bacterial, or parasitic diseases, inflammatory diseases including psoriasis and arthritis and atrial-ventricular malformations. Treatment of cancer includes, but is not limited to, killing cancer cells, slowing metastases, slowing or stopping angiogenesis, slowing or stopping the growth of the cancer cells or the size or mass of a tumor, making the cancer more responsive to a secondary therapy, such as radiation treatment. Treating an infectious disease includes, but is not limited to, reducing the length or severity of the infection, reducing morbidity, reducing mortality or killing the infectious agent. Treating an inflammatory disease includes, but is not limited to, reducing the amount or size of inflammation, reducing the severity of the inflammation, and reducing the length of the inflammatory outbreak.

The pH sensitive vesicles or liposomes may also comprise an agent selected from an imaging agent such as a fluorescent marker, a dye, a radiological marker or other tracking agent. These vesicles may be used in methods of tracking or determining the dosage or exposure to ionizing radiation. For example the tracking agent may be used as a visual aid to ensure that the proper dosage of ionizing radiation was administered to a subject to reach a desired site or cause a desired reaction.

Administration of the compositions described herein to a subject in accordance with the invention appears to exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity associated with the agent is seen.

It will be appreciated that the specific dosage administered in any given case will be adjusted in accordance with the compositions being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of the agent provided without a lipid vesicle delivery vehicle, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the compositions will reduce symptoms of the condition at least 10%, 20%, 30%, 40%, 50%, 60%, 70%, 80%, 90% or 100% compared to pre-treatment symptoms or symptoms is left untreated. It is specifically contemplated that pharmaceutical preparations and compositions may palliate or alleviate symptoms of the disease without providing a cure, or, in some embodiments, may be used to cure the disease or disorder.

Suitable effective dosage amounts for administering the compositions may be determined by those of skill in the art, but typically range from about 1 microgram to about 100,000 micrograms per kilogram of body weight of the agent weekly, although they are typically about 1,000 micrograms or less per kilogram of body weight weekly. In some embodiments, the effective dosage amount ranges from about 10 to about 10,000 micrograms per kilogram of body weight weekly. In another embodiment, the effective dosage amount ranges from about 50 to about 5,000 micrograms per kilogram of body weight weekly. In another embodiment, the effective dosage amount ranges from about 75 to about 1,000 micrograms per kilogram of body weight weekly. The effective dosage amounts described herein refer to total amounts administered, that is, if more than one agent is administered, the effective dosage amounts correspond to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks. The number of liposomes or vesicles in a dose will depend largely on the amount of the agent per liposome or per mL of the solution.

The following examples are meant only to be illustrative and are not meant as limitations on the scope of the invention or of the appended claims. All references cited herein are hereby incorporated by reference in their entireties.

EXAMPLES

Pharmaceuticals, therapeutics or other agents can be released from pH sensitive liposomes when the external or internal pH decreases depending on the liposomes. The liposomes are pH sensitive and include an organic halogen in the liposome. The pH of an organic halogen solution decreases upon X-ray irradiation. The decreased pH facilitates drug release by increasing the liposomal membrane permeability of the pH sensitive vesicles.

Materials and Methods pH sensitive liposomes which are stable at neutral pH but become destabilized at slightly acid pH were prepared as previously described by extrusion through polycarbonate filters (Hafez, 2000 and in International PCT Application No. PCT/US2010/029413). The liposomes were composed of phosphatidylethanolamine, distearoylphosphatidylcholine, cholesterol, and 1,2-distearoyl-sn-glycero-3-phosphoethanolamine-N-[methoxy(polyethylene glycol)-2000] in a molar ratio of 1:0.5:0.5:0.075 in unbuffered chloral hydrate ($C_2H_3Cl_3O_2$) solutions of IM, 0.5M, and 0.1 M, with or without addition of 0.1 M glucose (pH was adjusted to 7.1 for all samples). The fluorescent drug simulator, calcein, was added during liposome preparation at 5 mM concentration, sufficient for fluorescence self quenching. Control samples with identical composition but without glucose were prepared at the same time with the test samples. All test samples were irradiated with 6 MeV X-ray, 400 Rad, 2 minutes (therapeutic dose). The fluorescence as indicator of drug release was measured before and after irradiation with a Horiba fluorometer (Fluoromax 4P) in kinetics mode. The maximum release was estimated from the fluorescence measured upon complete membrane destabilization with 0.2% Triton X-100.

Results

Figure 2:
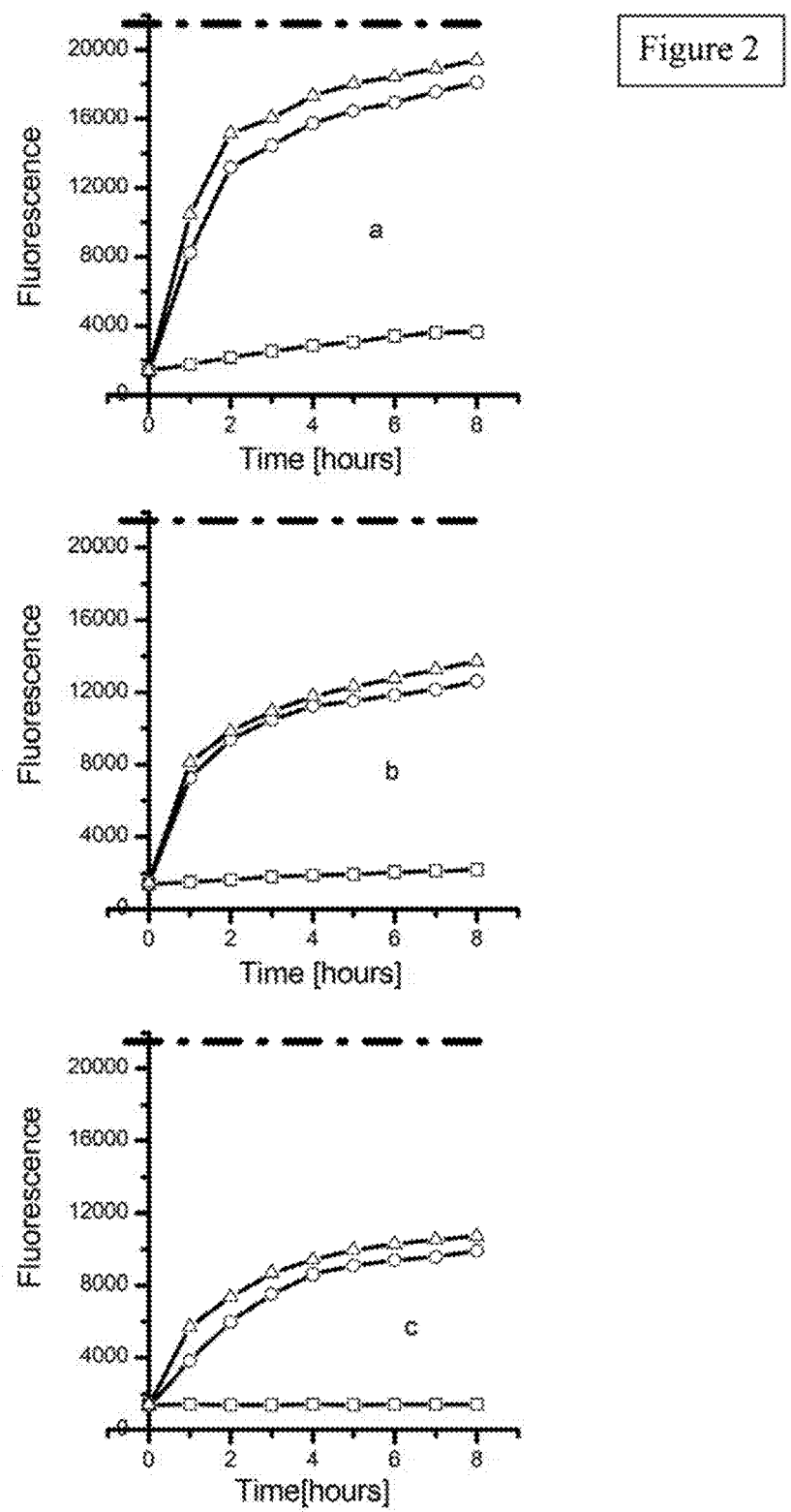
FIG. 2 is a set of graphs showing the release of a fluorescent marker, calcein, from liposomes after exposure to X-rays over time.

The results are presented in FIG. 2. The dashed line represents release of calcein after treatment of the vesicles with 0.2% Triton X-100 and is considered 100% release. All test samples indicated extensive calcein release upon irradiation. As a general rule, addition of glucose at 0.1 M increased slightly the efficiency of release for all samples, and this confirms previous experimentation showing that glucose addition facilitates pH decreases upon irradiation (Hilsenrod 1956). The non-irradiated sample containing IM chloral hydrate showed some calcein leakage at rest (FIG. 2a) and suggested that at this concentration the liposomes are not highly stable. The samples containing 0.5M (FIG. 2b) and 0.1 M (FIG. 2c) chloral hydrate showed a higher stability and minimal or no leakage at rest. Both the samples including 0.5M or 0.1 M chloral hydrate showed over 50% release of the calcein by 8 hours after the exposure to X-rays.

CONCLUSIONS

We demonstrated that X-ray radiation can control the release of drugs from pH sensitive liposomes containing organic halogen solutions. Further optimization will focus on using various lipid compositions for faster release and improved stability at rest and stability and controlled release in the context of a subject.

REFERENCES

1) Andrews, H. L., R. E. Murphy, et al. (1957). "Gel Dosimeter for Depth-Dose Measurements." *The Review of Scientific Instruments* 28(5): 329-332.
2) Andrews, H. L. and P. A. Shore (1950). "X-ray Dose Determinations with Chloral Hydrate." *The Journal of Chemical Physics* 18(9): 1165-1168.
3) Bisby, R., C. Mead, et al. (1999). "Photosensitive liposomes as' cages' for laser-triggered solute delivery: the effects of bilayer cholesterol on kinetics of solute release." *FEBS Letters* 463: 165-168.
4) Bisby, R., C. Mead, et al. (2000). "Active Uptake of Drugs into Photosensitive Liposomes and rapid release on UV Photolysis." *Photochemistry and Photobiology* 72(1): 57-61.
5) Bisby, R., C. Mead, et al. (2000). "Wavelength-Programmed Solute Release from Photosensitive Liposomes." *Biochemical and Biophysical Research Communications* 276: 169-173.
6) Freeman, G. R., A. B. Van Cleave, et al. (1953). "Irradiation of Aqueous Chloral Hydrate Solutions with $Co^{60}$ Gamma-Rays." *Canadian Journal of Chemistry* 32: 322-326.

7) Freeman, G. R., A. B. Van Cleave, et al. (1953). "Irradiation of One Molar Aqueous Chloral Hydrate Solution with Co$^{60}$-Gamma-Rays and Betatron X Rays." *Canadian Journal of Chemistry* 31: 1164-1172.
8) Hafez, I. M., S. Ansell, et al. (2000). "Tunable pH-Sensitive Liposomes Composed of Mixtures of Cationic and Anionic Lipids." *Biophysical Journal* 79: 1438-1446.
9) Harrington, K., G. Rowlinson-Busza, et al. (2000). "Pegylated Liposome-encapsulated Doxorubicin and Cisplatin Enhance the Effect of Radiotherapy in a Tumor Xenograft Model." *Clinical Cancer Research* 6: 4939-4949.
10) Hazemoto, N., M. Harada, et al. (1990). "pH-Sensitive Liposomes Composed of Phosphatidylethanolamine and Fatty Acid." *Chem. Pharm. Bull.* 38(3): 748-751.
11) Heusinger, H., R. J. Woods, et al. (1959). "Study of the Radiolysis of Bromal Hydrate Solutions Using $C^{14}$-labelled Bromal." *Canadian Journal of Chemistry* 37(7): 1127-1131.
12) Hilsenrod, A. (1956). "Irradiation of Chloral Hydrate Solutions." *Journal of Chemical Physics* 24: 917-918.
13) Kitano, H., Y. Akatsuka, et al. (1991). "pH-responsive liposomes which contain amphiphiles prepared by using lipophilic radical initiator." *Macromolecules* 24(1): 42-46.
14) Lee, R. J., s. Wang, et al. (1998). "The Effects of pH and Intraliposomal Buffer Strength on the rate of Liposome Content Release and Intracellular Drug Delivery." *Bioscience Reports* 18(2): 69-78.
15) Platford, R. F. and J. W. Spinks (1959). "Irradiation of Aqueous Chloral Hydrate With $Sr^{90}$-$Yr^{90}$ Beta Rays." *Canadian Journal of Chemistry* 37: 1022-1028.
16) Slepushkin, V. A., S. Simoes, et al. (1997). "Sterically Stabilized pH-sensitive Liposomes." *The Journal of Biological Chemistry* 272(4): 2382-2388.
17) Woods, R. J. and J. W. Spinks (1957). "The Action of Co$^{60}$ Gamma Rays and of Fenton Reagent on Aqueous Bromal Hydrate Solutions." *Canadian Journal of Chemistry* 35: 1475-1486.
18) Woods, R. J. and J. W. Spinks (1960). "The Radiolysis of Some Organic Halogen Compounds in Aqueous Solution." *Canadian Journal of Chemistry* 38: 77-93.

We claim:

1. A pH sensitive lipid vesicle composition configured for the controlled release of an agent upon exposure to ionizing radiation, the composition comprising:
   a lipid layer, the lipid layer comprising a pH sensitive phospholipid selected from the group consisting of a phosphatidylethanolamine, a phosphatidylcholine, and a combination thereof, and
   an aqueous medium, the aqueous medium comprises the agent and an organic halogen capable of interacting with ionizing radiation to increase the acidity of the aqueous medium,
   wherein the organic halogen is selected from chloral hydrate and bromal hydrate and has a concentration between 0.01 M and 2 M in the aqueous medium within the vesicle.

2. The composition of claim 1, wherein the pH sensitive phospholipid is selected from the combination of the phosphatidylethanolamine and the phosphatidylcholine.

3. The composition of claim 1, wherein the lipid layer further comprises a member selected from a lipid anchored polyethylene glycol, cholesterol, a targeting molecule, a pH sensitive polymer, a polypeptide capable of localizing in the lipid layer, and any combination thereof.

4. The composition of claim 3, wherein the lipid layer comprises the lipid anchored polyethylene glycol, cholesterol, or both the lipid anchored polyethylene glycol and cholesterol.

5. The composition of claim 3, wherein the targeting molecule is selected from a targeting polypeptide, a folate receptor, an antibody, and any combination thereof.

6. The composition of claim 3, wherein the pH sensitive polymer comprises a pH sensitive moiety selected from the group consisting of methylacrylic acid, ethylacrylic acid, propylacrylic acid, butylacrylic acid, and any combination thereof.

7. The composition of claim 1, wherein the agent is selected from a group consisting of a cancer therapeutic agent, a polypeptide, a toxin, a radiotherapeutic agent, a radiosensitizing agent, an angiogenesis inhibitor, an imaging agent, and any combination thereof.

8. The composition of claim 3, wherein the molar ratio of the pH sensitive lipid, the lipid anchored polyethylene glycol, cholesterol, the targeting molecule, the pH sensitive polymer, and the polypeptide capable of localizing in the lipid layer is configured to initiate sustained release of the agent following exposure to ionizing radiation while sealing the lipid layer prior to exposure to ionizing radiation at an initial pH.

9. The composition of claim 1, wherein the aqueous medium has a concentration of organic halogen configured to initiate sustained release of the agent following exposure to ionizing radiation while sealing the lipid layer prior to exposure to ionizing radiation at an initial pH.

10. The composition of claim 1, wherein the composition is configured release at least 25% of the agent within 4 hours of interacting with ionizing radiation.

11. The composition of claim 1, wherein the composition is configured to release at least 50% of the agent within 8 hours of interacting with ionizing radiation.

12. A pH sensitive lipid vesicle composition configured for the controlled release of an agent upon exposure to ionizing radiation, the composition comprising:
   a lipid layer, the lipid layer comprising a pH sensitive phospholipid selected from the group consisting of a phosphatidylethanolamine, a phosphatidylcholine, and a combination thereof, a lipid anchored polyethylene glycol, and cholesterol, and an aqueous medium, the aqueous medium comprises the agent and an organic halogen capable of interacting with ionizing radiation to increase the acidity of the aqueous medium,
   wherein the organic halogen is selected from chloral hydrate and bromal hydrate and has a concentration between 0.01 M and 2 M in the aqueous medium within the vesicle.

13. The composition of claim 12, wherein the pH sensitive phospholipid is selected from the combination of the phosphatidylethanolamine and the phosphatidylcholine.

14. The composition of claim 12, wherein the molar ratio of the pH sensitive lipid, the lipid anchored polyethylene glycol, and cholesterol in the lipid layer is configured to initiate sustained release of the agent following exposure to ionizing radiation while sealing the lipid layer prior to exposure to ionizing radiation at an initial pH.

15. The composition of claim 12, wherein the aqueous medium has a concentration of organic halogen configured to initiate sustained release of the agent following exposure to ionizing radiation while sealing the lipid layer prior to exposure to ionizing radiation at an initial pH.

16. A method for the localized release of an agent within a subject, the method comprising:

administering a pH sensitive lipid vesicle composition as in claim 1 to a subject and exposing a portion of the subject to ionizing radiation whereby interaction of the composition to the ionizing radiation within the exposed portion of the subject initiates the release of agent from the composition.

17. The method of claim 16, wherein the molar ratio of the pH sensitive lipid in the lipid layer is configured to initiate sustained release of the agent following exposure to ionizing radiation while sealing the lipid layer prior to exposure to ionizing radiation within the subject.

18. The method of claim 16, wherein the aqueous medium has a concentration of organic halogen configured to initiate sustained release of the agent following exposure to ionizing radiation while sealing the lipid layer prior to exposure to ionizing radiation within the subject.

19. The method of claim 16, wherein the lipid layer further comprises a lipid anchored polyethylene glycol and cholesterol.

* * * * *